(12) United States Patent
Guo

(10) Patent No.: US 8,976,359 B2
(45) Date of Patent: Mar. 10, 2015

(54) NANOSTRUCTURE DIFFRACTION GRATINGS FOR INTEGRATED SPECTROSCOPY AND SENSING

(71) Applicant: Junpeng Guo, Madison, AL (US)

(72) Inventor: Junpeng Guo, Madison, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 13/716,122

(22) Filed: Dec. 15, 2012

(65) Prior Publication Data

US 2014/0168651 A1 Jun. 19, 2014

(51) Int. Cl.

| G02B 5/18 | (2006.01) |
| G01N 21/55 | (2014.01) |
| G01N 21/552 | (2014.01) |
| G01N 21/65 | (2006.01) |

(52) U.S. Cl.
CPC ............... *G02B 5/18* (2013.01); *G01N 21/554* (2013.01); *G01N 21/658* (2013.01)
USPC .......................................... 356/445; 356/301

(58) Field of Classification Search
USPC ............ 356/445, 300, 301, 317, 319; 385/12, 385/147, 129; 435/287.2
See application file for complete search history.

(56) References Cited

U.S. PATENT DOCUMENTS

| 6,784,999 | B1* | 8/2004 | Tao et al. ...................... 356/445 |
| 6,867,865 | B2* | 3/2005 | Vaupel ......................... 356/445 |
| 7,756,365 | B2* | 7/2010 | Cunningham et al. .......... 385/12 |
| 8,076,090 | B2* | 12/2011 | Fang et al. ................... 435/7.21 |
| 8,508,744 | B2* | 8/2013 | Valsesia et al. ............... 356/445 |
| 2007/0252982 | A1* | 11/2007 | Wang et al. .................. 356/301 |
| 2008/0130003 | A1* | 6/2008 | Kuroda et al. ................ 356/445 |
| 2008/0278728 | A1* | 11/2008 | Tetz et al. ..................... 356/445 |
| 2008/0316490 | A1* | 12/2008 | Yen et al. ...................... 356/445 |
| 2009/0187350 | A1* | 7/2009 | Chau et al. ....................... 702/19 |
| 2012/0002203 | A1* | 1/2012 | Romanato et al. ............ 356/369 |
| 2012/0026493 | A1* | 2/2012 | Stuke et al. ................... 356/301 |

* cited by examiner

*Primary Examiner* — Sang Nguyen
(74) *Attorney, Agent, or Firm* — Maynard Cooper & Gale, P.C.; Jon E. Holland

(57) ABSTRACT

The present disclosure pertains to metal or dielectric nanostructures of the subwavelength scale within the grating lines of optical diffraction gratings. The nanostructures have surface plasmon resonances or non-plasmon optical resonances. A linear photodetector array is used to capture the resonance spectra from one of the diffraction orders. The combined nanostructure super-grating and photodetector array eliminates the use of external optical spectrometers for measuring surface plasmon or optical resonance frequency shift caused by the presence of chemical and biological agents. The nanostructure super-gratings can be used for building integrated surface enhanced Raman scattering (SERS) spectrometers. The nanostructures within the diffraction grating lines enhance Raman scattering signal light while the diffraction grating pattern of the nanostructures diffracts Raman scattering light to different directions of propagation according to their wavelengths. Therefore, the nanostructure super-gratings allows for the use of a photodetector array to capture the surface enhanced Raman scattering spectra.

9 Claims, 16 Drawing Sheets

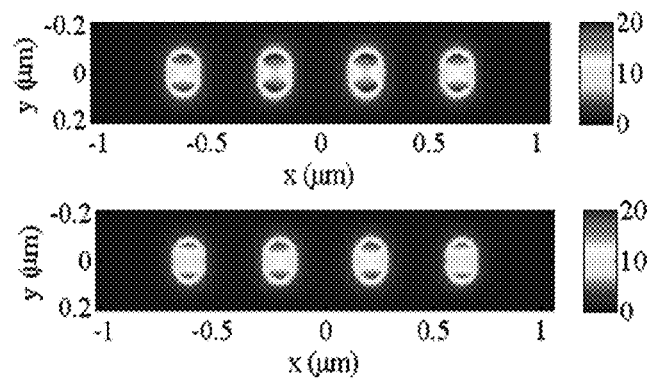
*FIG. 13A*
*FIG. 13B*
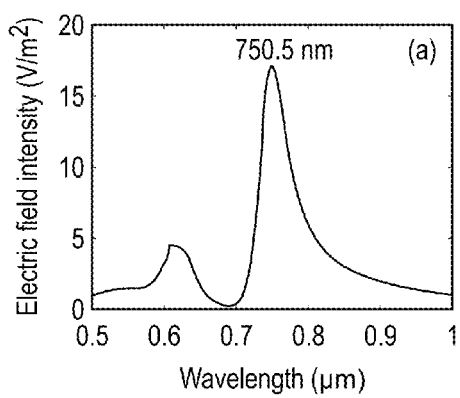
*FIG. 14A*
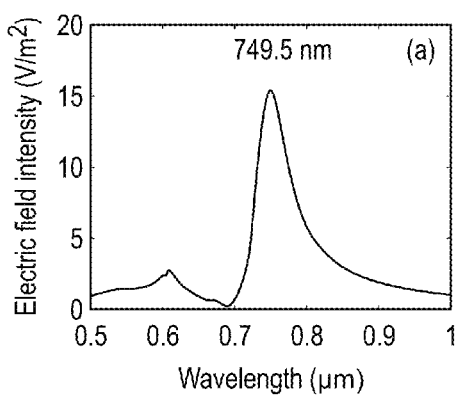
*FIG. 14B*

NANOSTRUCTURE DIFFRACTION GRATINGS FOR INTEGRATED SPECTROSCOPY AND SENSING

GOVERNMENT INTEREST

This invention was made with government support under contract NNX07-AL52A, awarded by the National Aeronautics and Space Administration (NASA), and contract NSF-0814103, awarded by the National Science Foundation (NSF). The Government has certain rights in the invention.

RELATED ART

Spectroscopy and most spectroscopy based chemical sensing techniques rely on spectrometers to perform spectral measurement of optical radiations. One type of optical spectrometer relies on diffraction gratings to separate spectral frequency components of radiations. Diffraction gratings often comprise periodically arranged metal or dielectric lines on transparent substrates which serve as supporting materials. Optical radiations of different frequencies can be spatially separated and measured by using photodetector arrays.

The advancement of nanotechnology has created a new class of chemical and biological sensors that rely on the resonance shift of metal and dielectric nanostructure devices as the sensing transduction mechanism. One well investigated nanostructure optical resonance type is localized surface plasmon resonance (LSPR), which occurs in metal nanostructures. LSPR is the collective oscillation of free electrons (known as surface plasmons) in metal nanostructures. At a certain frequency, the plasmons resonate with incident light, resulting in strongly enhanced electromagnetic field near the nanostructure surface. Resonance frequencies in nanostructures change when chemical or biochemical agents bind onto on surface of the nanostructure. Traditionally, optical spectrometers are used to perform the spectral measurements for determining the resonance frequency shift. One type of chemical sensor relies on measurement of the resonance frequency change using optical spectrometers.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 13A illustrates an electric field intensity distribution profile on the near field plane 20 nm above the metal surface at 750.5 nm wavelength.

FIG. 13B illustrates an electric field intensity distribution profile on the near field plane 20 nm above the metal surface at 760.5 nm wavelength.

FIG. 14A shows a graph of near electric field intensity versus the wavelength at the top center of an inner nanohole aperture within the super-period grating period.

FIG. 14B shows a graph of near electric field intensity versus the wavelength at the top center of an outer nanohole aperture within the super-period grating period.

DETAILED DESCRIPTION

The disclosure described herein is generally directed to nanostructures in the sub-wavelength scale within the grating lines of diffraction gratings. The nanostructures within the grating lines have designed surface plasmon resonances for metallic nanostructures or optical resonances for dielectric nanostructures. The resonance frequencies shift as the nanostructure surfaces interact with chemical and biological agents of interest. Measurement of surface plasmon resonance or optical resonance is accomplished by measuring either the spectrum of the reflected light or the spectrum of transmitted light, using optical spectrometers. The presently disclosed device and method eliminates the use of external optical spectrometers when measuring the resonance shift caused by the presence of chemical and biological agents. The present disclosure describes the measurement of resonance frequency and the simultaneous shift when utilizing the combination of a nanostructure diffraction grating and a photodetector array.

The grating periods of diffraction gratings are larger than the wavelengths to be measured, typically from several to several hundred times of the longest wavelength to be measured. According to the diffraction theory, different spectral components of radiation propagate to different directions following the equation:

$$\mathrm{Sin}(\theta) = m\frac{\lambda}{P}, \quad (1)$$
$$m = 0, \pm 1, \pm 2, \ldots$$

where θ is the angle of the diffraction, m is the order of the diffraction, λ is the wavelength, and P is the diffraction grating period. Equation 1 is relevant to normal light incidence to the grating surface. If the incident angle is not normal to the surface of the diffraction grating, the diffracted angle θ must be corrected accordingly. The diffraction grating lines can be made of metal, dielectric, or other materials. The grating lines can be flat or tilted such as in blazed gratings.

Figure 1:
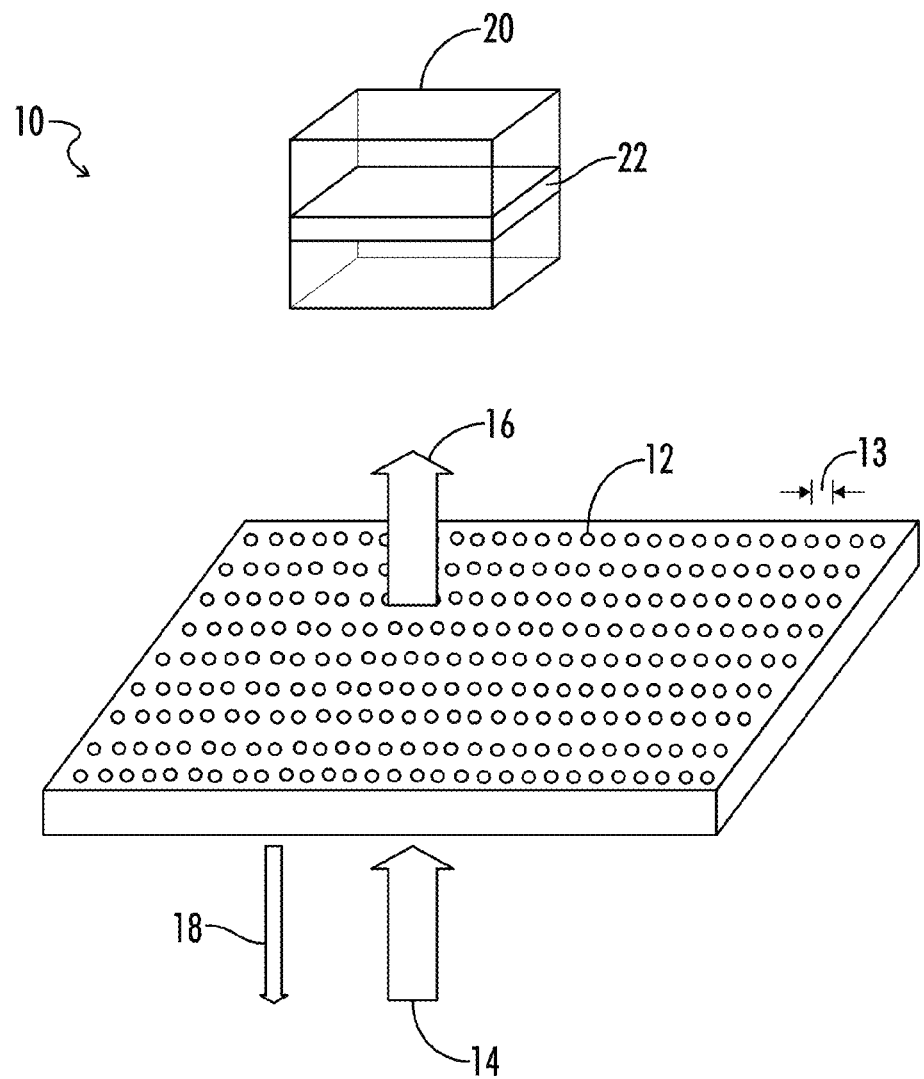
FIG. 1 illustrates a subwavelength period nanohole array.

FIG. 1 depicts a subwavelength nanohole array in a thin metal (such as gold or silver) film 12. The enhanced transmission 16 of incident light 14 through the subwavelength period nanoholes 12 occurs when the frequency of incident light 14 is tuned to the resonance frequency of the periodic nanohole array 12. The local plasmon resonance in the periodic nanoholes contributes to the enhanced light transmission 16 through the nanohole array 10. Enhanced optical transmission and the underlined surface plasmon resonance can only be measured in either the transmission 16 or the reflection 18 because the period of the nanoholes 12 in the array 10 is smaller than the wavelengths to be measured.

The resonance frequencies in metal nanostructures 10 are generally measured by using an optical spectrometer 20 containing a diffraction grating 22 to measure the reflection or the transmission from the nanostructure device. Traditional optical diffraction gratings 22 are comprised of metal or dielectric lines placed in periodic patterns with the width 13 greater than the wavelength of the light to be measured. The grating lines are arranged periodically on transparent substrates.

In contrast, the present disclosure illustrates nanostructures of the subwavelength scale within the grating lines of a traditional diffraction grating. The nanostructures within the grating lines have surface plasmon resonances or non-plasmon optical resonances. The resonance frequencies shift as the nanostructure surfaces interact with chemical and biological agents to be measured. The modified resonance spectra are angularly and spatially separated by the diffraction grating. The nanostructures have feature sizes smaller than the wavelengths of radiations. These nanostructure diffraction gratings enhance the capability for spectral measurements and also significantly reduce the physical dimension size of the sensor instruments.

Figure 2:
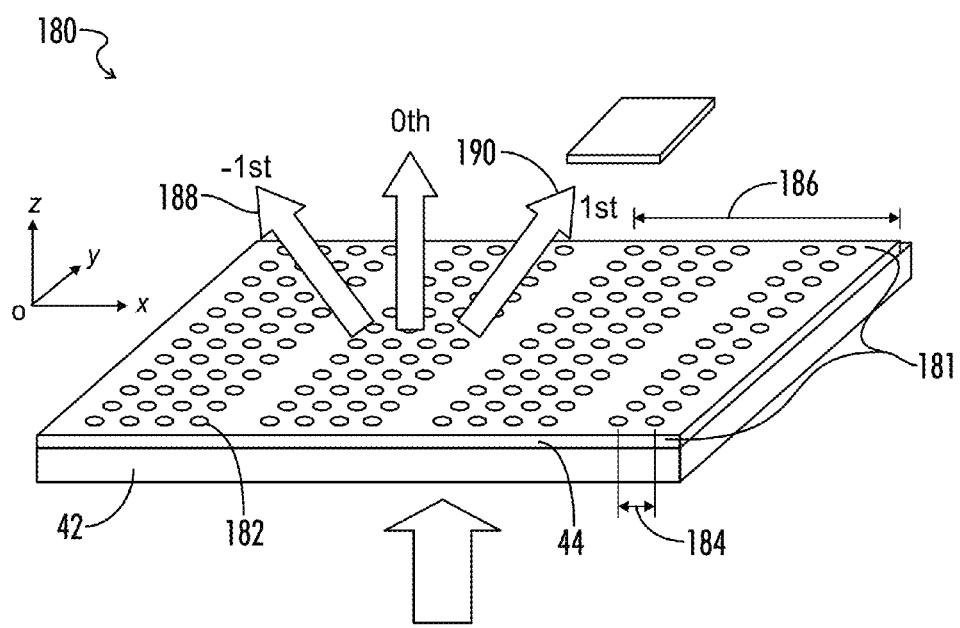
FIG. 2 illustrates a super-period nanohole array diffraction grating.

FIG. 2 illustrates a nanohole array diffraction grating 180. The grating 180 comprises a substrate layer 42 composed of a transparent material. As used herein, a transparent material is a material with the physical properly of allowing light to pass through the material without being absorbed. There are a number of suitable transparent substrate materials, for instance quartz, plastic or glass. It is to be understood that other transparent materials may be used as the substrate layer 42 of the present disclosure. A grating layer 44 is next deposited on top of the substrate layer 42. In one exemplary embodiment, the grating layer 44 comprises of a planar metal, such as gold or silver, or a dielectric material. Suitable metal surfaces in accordance with the present disclosure include various noble metals, e.g. gold, silver or platinum, as well as base metals such as copper, aluminum, chromium, and also various metal alloys, etc. The metal may be provided in the form of a film, preferably a thin film.

The grating 180 comprises a series of diffraction grating lines 181. Each grating line 181 consists of an array of sub-wavelength sized nanoholes 182 located within the grating lines 181. Although the grating 180 in FIG. 2 illustrates an array of nanoholes, it is to be understood that these nanostructures may take the form of any shape, whether recessed or bored into the grating surface (i.e., a hole or a trench) or fixed upon and protruding from the grating surface (i.e., a raised circle, line or square). By way of example, the nanostructure can have circular, square, rectangular, elliptical or triangular shapes, provided that the dimensions of the shape are smaller than the wavelengths to be measured. Each diffraction grating line 181 has a finite number of nanoholes 182 in one dimension and infinite (practically very large) number of nanoholes 182 in another dimension. The nanohole array grating lines 181 are arranged periodically with a diffraction grating period of 186. The diffraction grating period 186 is larger than the wavelengths being measured, typically several times of the longest wavelength to be measured. This produces angularly dispersed diffractions. Different wavelengths are diffracted to different directions following the diffraction grating theory described by equation 1 for the normal incidence of light. In contrast, the width of nanoholes 182 is sized smaller than the wavelength of the incident light, thus producing a surface plasmon resonance. Diffraction orders are generated when light is incident to the grating 180. The diffracted radiations are angularly dispersed in space due to the diffraction, i.e. spectral components of different wavelengths propagate to different directions in space. A photodetector array is used to capture the spectral components of diffracted light.

Figure 3A:
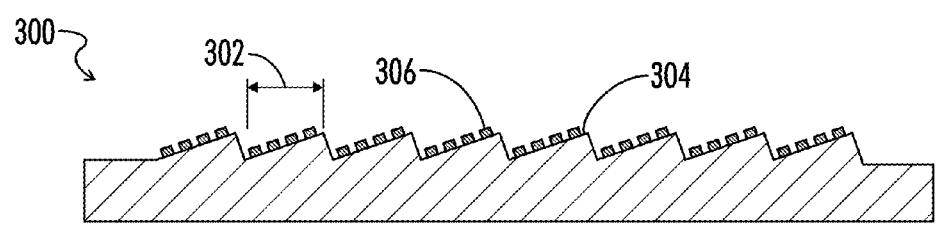
FIG. 3A illustrates a cross sectional view of a blazed nanostructure diffraction grating.
Figure 3B:
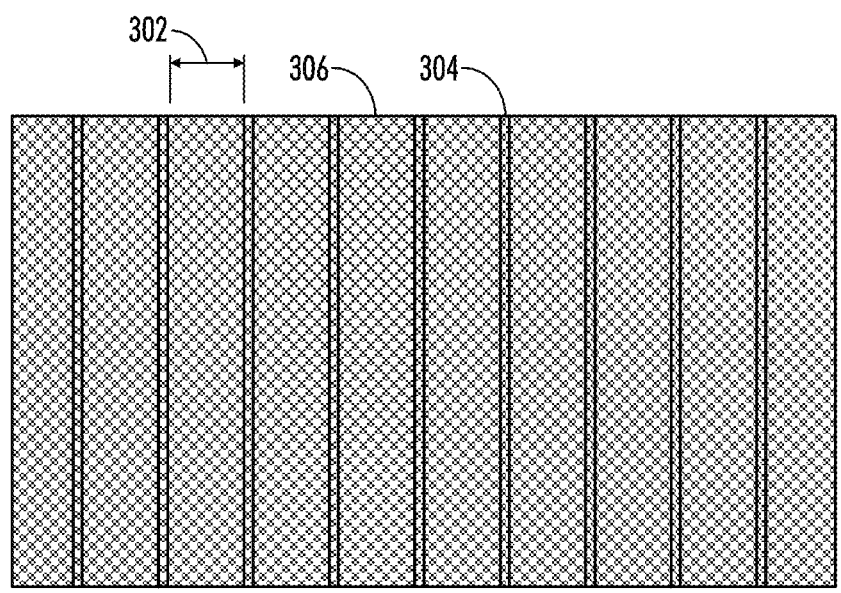
FIG. 3B illustrates a top view of a blazed nanostructure diffraction grating.

FIGS. 3A and 3B illustrate an additional embodiment of a nanostructure diffraction grating of the present disclosure. FIG. 3A shows a cross-sectional view of a blazed diffraction grating 300. The blazed grating 300 has constant line spacing or period 302 which determines the magnitude of the wavelength dispersion caused by the grating. The grating lines 304 possess a triangular, sawtooth-shaped cross section, thus forming a step structure. The steps are tilted at the so called "blaze angle" with respect to the grating surface. Subwavelength sized nanostructures 306 are located onto the upper surface of the blazed grating. FIG. 3B shows a top view illustration of the distribution of nanostructures 306. The blaze grating period 302 is larger than the wavelengths being measured, typically several times of the longest wavelength to be measured. This produces angularly dispersed diffractions. Different wavelengths are diffracted to different directions following the diffraction grating theory. In contrast, nanostructures within the blazed grating lines 306 are sized smaller than the wavelength of the incident light, thus producing surface plasmon or non-plasmon resonance. Diffraction orders are generated when light is incident to the grating 300. The diffracted radiations are angularly dispersed in space due to the diffraction, i.e. spectral components of different wavelengths propagate to different directions in space. A photodetector array can be used to measure the spectral components of diffracted light.

In the embodiment described above in reference to FIGS. 2, 3A and 3B the nanostructures, or nanoholes, may be randomly arranged. In an additional embodiment, the nanostructures are arranged in a repeating, periodic fashion herein referred to as a "period". Referring again to FIG. 2, the nanoholes 182 may be positioned so as to provide a period 184 which is smaller than the wavelengths of diffracted light to be measured. As described above, the diffraction grating lines 181 have a period 186 which is larger than the wavelength of the diffracted light to be measured. In the embodiment illustrated in FIG. 2, the small period 184 is arranged within the large period 186. The large grating period 186 is several times the size of the small period 184.

Figure 4:
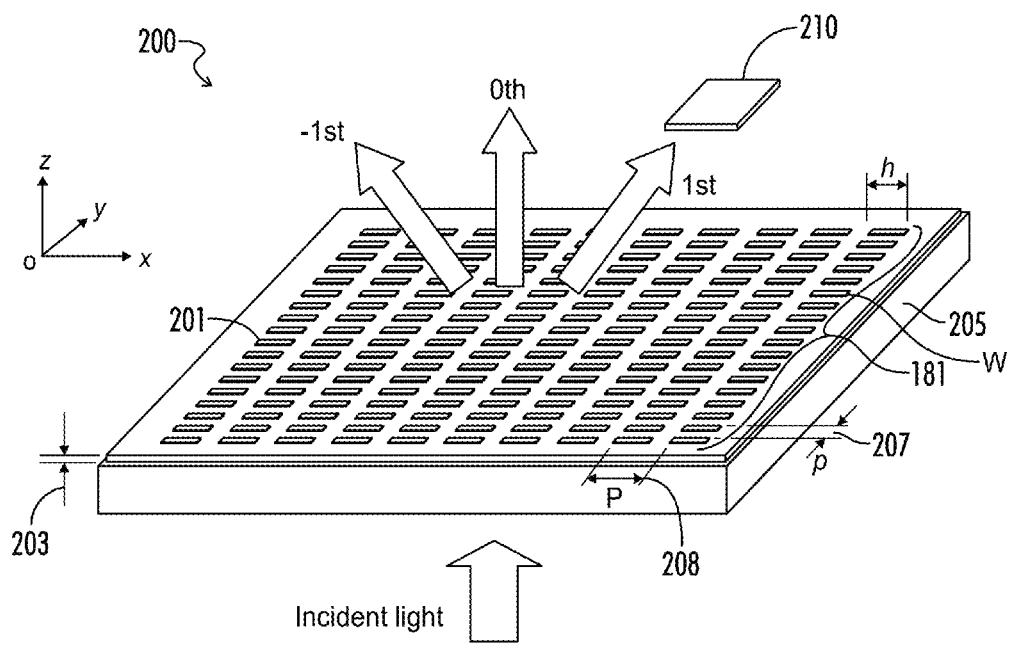
FIG. 4 illustrates a rectangular nano-aperture array diffraction grating.

FIG. 4 illustrates a two dimensional elongated nanoaperture array diffraction grating 200. The nanoapertures 201 are etched into the metal or dielectric film 181 of a thickness 203. In one example, the apertures 202 may have rectangular or elliptical shapes. The grating 200 is on an optically transparent substrate 205. The nano-apertures 201 have a subwavelength period 207 in the y direction and a diffraction grating period 208 in the x direction. The diffraction grating period 208 is larger than the wavelengths of the diffracted light being measured, typically several times of the longest wavelength to be measured. The diffractions propagate in the x-z plane. Due to the intrinsic angular dispersion of diffractions caused by the diffraction grating with the period 208, the resonance in diffraction orders can be measured with a photodetector array 210. One example of a photodetector array is a one-dimensional linear photodetector array or a two dimensional photodetector array (e.g., a charged coupled device ("CCD")). The polarization of the incident light is in the y direction to effectively excite the resonances in the nano-aperture array structure 200. No additional optical spectrometers are needed to measure the resonance in the nanostructure device.

Figure 5:
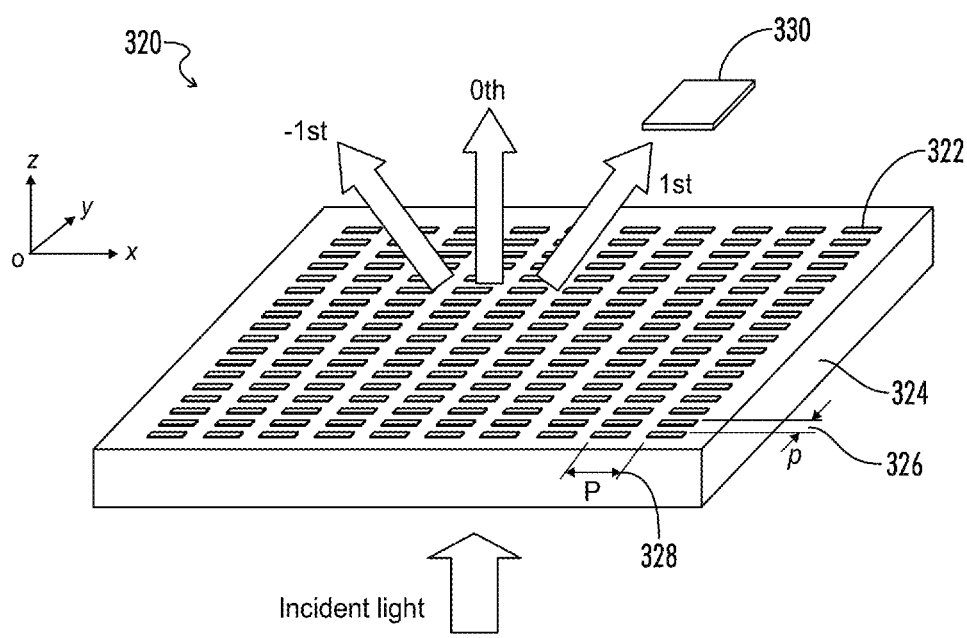
FIG. 5 illustrates a nanogrid array diffraction grating.

FIG. 5 illustrates an additional embodiment of a nanostructure optical grating. This two dimensional nanogrid array grating 320 comprises raised nanostructures 322 which protrude above the upper surface of the array 320. In one example, the nanostructures 322 can have rectangular or elliptical shapes. The grating 320 is supported by an optically transparent substrate 324. The nanostructures 322 have a subwavelength period 326 in the y direction and a diffraction grating period 328 in the x direction. The diffraction grating period 328 is larger than the wavelengths of the diffracted light being measured, typically several times of the longest wavelength to be measured. Because the grating period in the y-direction is smaller than the wavelengths, no diffractions propagate in the y-z plane. The diffractions propagate in the x-z plane. Due to the intrinsic angular dispersion of diffractions caused by the diffraction grating with the diffraction grating period 328, the optical resonance in the nanostructure device can be measured in one of the diffraction orders with a photodetector array 330. One example of a photodetector array is a one-dimensional linear photodetector array or a two dimensional photodetector array (e.g., a CCD). The polarization of the incident light should be in the y direction to effectively excite the optical resonances in the nanogrid array structure 320. No additional spectrometers are needed to measure the resonance in the nanostructure grating device.

Figure 6:
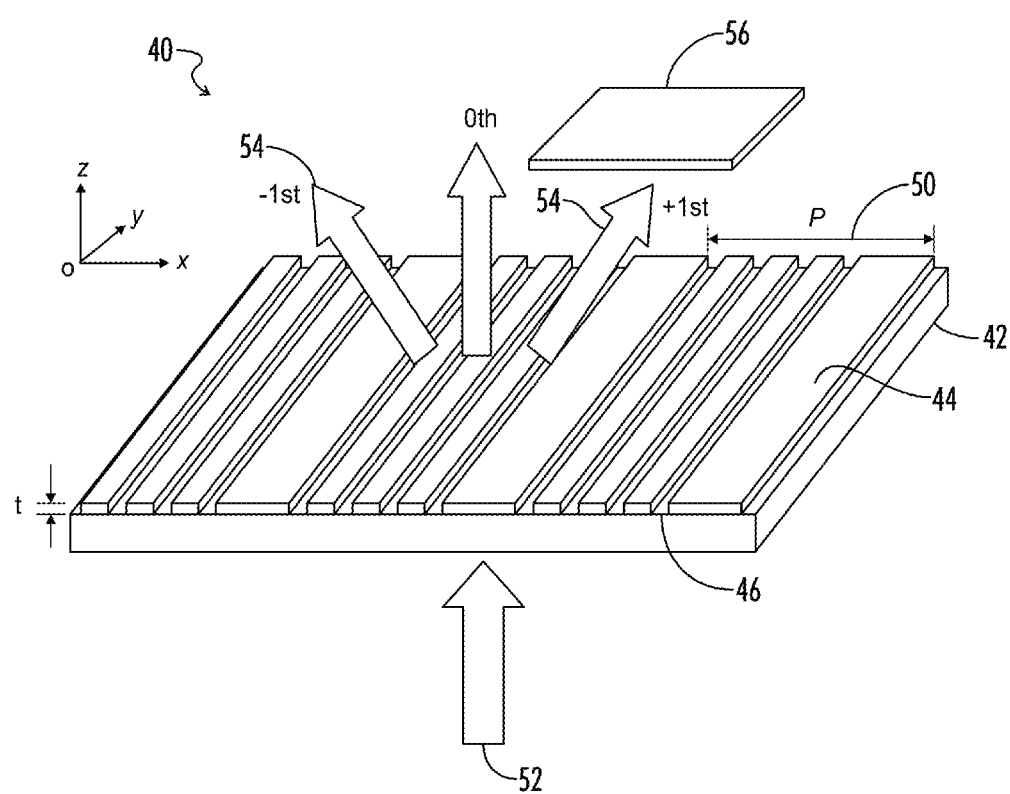
FIG. 6 illustrates a super-period nanoslit array grating with a small nano-grating period and a large diffraction grating period.

In an additional embodiment of the present disclosure, FIG. 6 illustrates a dual periodic nanoslit array 40. The nanoslits 46 comprise trenches or grooves etched into the grating surface 44. Nanoslits 46 are arranged periodically with a large period 50 above the wavelength of interest. The large period 50, also referred to as a "super-period," is created by periodically removing nanoslits 46 from a periodic nanoslit array 10. The super-period 50 functions as a diffraction grating period which is larger than the wavelength of interest. Because of the super-period 50 structure, surface plasmon radiations from the nanostructure arrays 40 can be measured from the non-zeroth order diffractions (i.e., the first order diffraction). Due to the intrinsic angular dispersion of diffractions, the resonance spectrum can be measured with a linear photodetector array or CCD 56 without using an external optical spectrometer.

Figure 7:
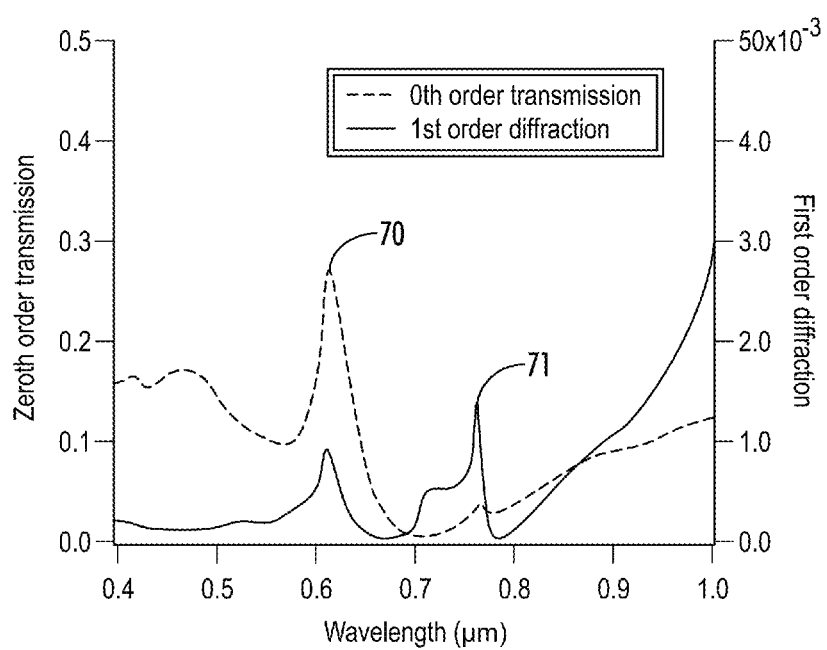
FIG. 7 illustrates the calculated spectra of the zero-order transmission and the first order diffraction from a super-period metal nanoslit grating.

The transmission and diffraction from the super-period nanostructure 40 can be obtained by solving Maxwell's equations. FIG. 7 illustrates the calculated spectra of the zero-order transmission and the first order diffraction from the super-period gold nanostructure 40 upon the normal incidence with the incident polarization perpendicular to the metal nanoslits 46. The sharp transmission peak 70 at 0.612 micron wavelength corresponds to the surface plasmon resonance that causes the enhanced zeroth-order transmission (dashed line) in the device. FIG. 7 illustrates that the spectral peak wavelength in the first order diffraction spectrum (solid line) is about the same wavelength of the spectral peak of the zeroth order transmission. An additional surface plasmon resonance in the device is observed in the zeroth order transmission and in the first order diffraction at 0.762 micron wavelength (71). This resonance does not exist in the regular period gold nanoslit array. It is due to the surface plasmon resonance in the large period grating 50. By using a linear photodetector array, the resonances in the nanostructure device can be obtained by measuring the spatially and spectrally dispersed first order diffraction from the nanostructure grating device. The super-period metal nanoslit array 40 itself supports localized surface plasmon resonance and performs the spectral analysis simultaneously.

In an additional embodiment, any of the above-described nanostructures may be utilized to study molecular binding interactions between free analyte molecules in solution and probe molecules which are linked to or immobilized on to the nanostructure grating surface. This embodiment contemplates one or more biomolecules attached to the nanostructure grating surface. For the purposed of this disclosure, "biomolecules" include, but are not limited to, single and double-stranded nucleic acids, oligonucleotides, proteins and protein fragments, amino acids, peptides, antibodies, antigens, viruses, virus fragments, hormones and small molecules such as drugs. The biomolecules may be attached directly to the grating. Alternatively, or in addition, the biomolecules may be attached to the grating via a number of chemical linker and spacer moieties. The attached biomolecules are then exposed to a test sample containing additional biomolecules (analytes) in free solution. Binding of an analyte to an immobilized biomolecule attached to the nanostructure grating 42 will cause changes in the local index of refraction, thus changing the resonance frequencies of the local surface plasmons. This shift of the local plasmon resonance frequency can be easily detected by the photodetector array, i. e. the CCD 56. The measurement of this optical resonance shift identifies the existence of chemical or biological agents on the nanostructure surface 40. This is a direct method of detection which avoids the drawbacks of labels. This elimination of the need for labeling is important for at least two reasons. First, it eliminates the need to chemically modify the biomolecule and the concomitant concern that the label might alter or modify the biomolecules activity or behavior. Second, biomolecules in complex mixtures (such as nuclear extracts) can be studied directly without having to purify them and attempt to label them in the mixture.

In an additional embodiment of the disclosure, any of the presently disclosed nanoslit arrays may be utilized to observe the time-dependent binding interaction between two biomolecules. The kinetics of molecular binding events may be studied by measuring the change of the local plasmon resonance frequency over time. When an analyte with high affinity to the immobilized biomolecule is introduced, binding events can be observed by monitoring the shift of the resonance frequency. An initial rapid change of the local plasmon resonance frequency can be observed as analyte begins to bind to the many available binding sites (i.e., attached biomolecules). While sample analyte is continually delivered to the nanostructure grating 42, analyte molecules continue to bind, thus lowering the available number of binding sites (attached biomolecules). The shift of the local plasmon and optical resonance frequency then levels off as the system reached equilibrium.

In an alternate embodiment, the present invention is directed to integrated surface enhanced Raman scattering spectroscopy (SERS) measurement based on nanostructure metal or dielectric diffraction gratings. The integrated SERS spectrometers rely on patterned nanostructure diffraction gratings. The patterned nanostructure diffraction gratings have two functions: (1) the nanostructures within the diffraction grating lines enhance the Raman scattering light; (2) the diffraction grating pattern of the patterned nanostructures diffracts Raman scattering light to different directions of propagation according to their wavelengths. A linear photodetector array is used to capture the spectra of the Raman scattering light because of the angular dispersion of the diffracted Raman scattering light.

Raman scattering is a spectroscopic technique used to observe vibrational, rotational, and other low-frequency modes in molecules. It relies on inelastic scattering, or Raman scattering, of monochromatic light, usually a laser in the visible, infrared, or ultraviolet range. The laser light interacts with molecular vibration modes, other excitations in the system, resulting in the energy of the photons being shifted up or down. The shift in energy gives information about the vibrational modes in the system. Typically, a sample is illuminated with a laser beam. Raman scattering light from the illuminated spot is collected with a lens and sent to an optical spectrometer. Scattered light at the wavelength of the excitation laser is filtered out with a rejection optical notch filter, while the rest of the collected light is measured by an optical spectrometer.

The presently disclosed SERS spectrometer and the accompanying nanostructures may be used to identify particular biological and chemical agents. Each molecule has a unique Raman scattering spectral signature. Measurement of this shift can be used to identify specific molecules or analytes. Specifically, the nanostructure is utilized in an integrated surface enhanced Raman scattering spectrometer. Surface enhanced Raman scattering spectroscopy is a label free detection technique that reveals molecular spectral "signatures." SERS is a powerful sensing technique that has many applications in material analysis and sensing.

Spontaneous Raman scattering is typically very weak, and as a result the main difficulty of Raman spectroscopy is separating the Raman scattered light from the intense Rayleigh scattered laser light. As a result, narrow spectral band rejection optical filters are needed to block the Rayleigh scattered light of the same wavelength of the excitation laser before the Raman scattering signals are collected by spectrometers.

Figure 17:
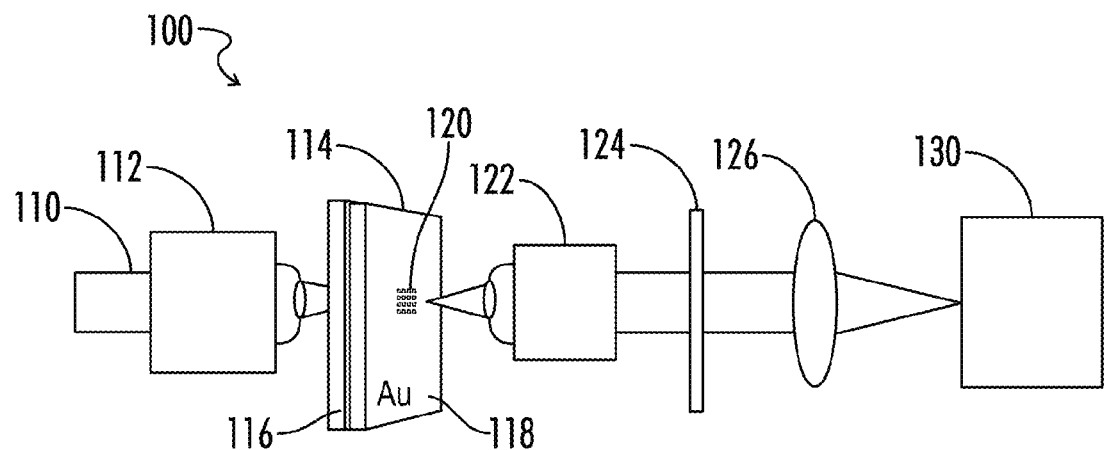
FIG. 17 illustrates a traditional surface enhanced Ramen spectrometer optical system setup.

A traditional optical setup 100 for Raman scattering spectroscopy measurement is illustrated in FIG. 17. A laser 110 is focused by a focal objective lens 112. The narrow bandwidth laser 110 is used to excite chemical or biological molecules on a nanostructured metal surface 114 to generate surface enhanced Raman scattering light. The nanostructure 114 comprises a substrate layer 116 composed of a transparent material, for example glass. The nanostructure surface layer 118 contains metal nanostructures (periodic or random) 120 on the surface.

Referring again to FIG. 17, the Raman scattering light produced by the laser 110 have Raman spectra which are uniquely determined by the molecules. Raman scattering light is directed through a second lens 122, filtered through an optical rejection notch filter 124, focused with a third lens 126, collected and sent to an optical spectrometer 130. The optical rejection filter 124 is used to reject the strong scattered light of the same wavelength as the excitation laser light 110. Because of the need for the optical rejection filters to remove incident laser light, current surface enhanced Raman spectrometers are expensive, bulky, and mainly used in laboratory environments.

Figure 18:
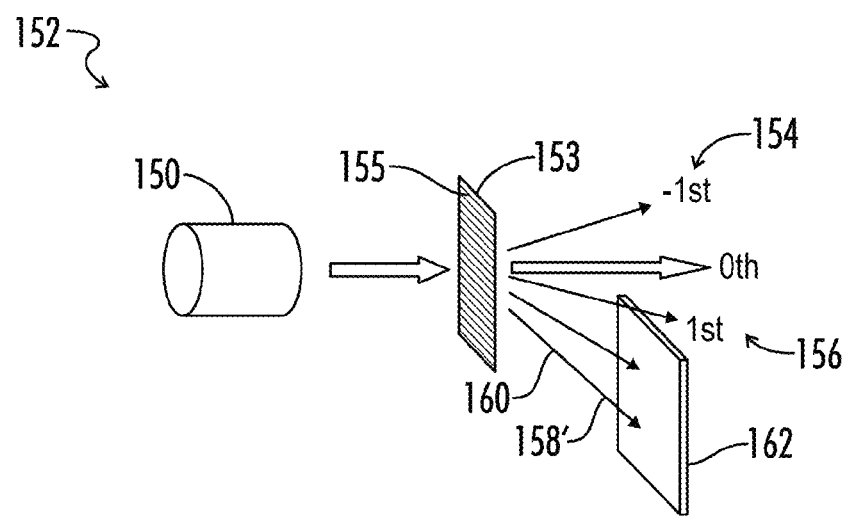
FIG. 18 illustrates the integrated nanostructure surface enhanced Raman spectrometer with the disclosed nanostructure diffraction grating.

The presently disclosed integrated SERS spectrometer comprising a patterned nanostructure diffraction grating 152 is schematically illustrated in FIG. 18. A narrow line-width laser 150 is incident to the grating containing patterned metal nanostructures (nanodots, nanoholes, nanoslits, etc.) 152. In one embodiment, the grating 152 is comprised of metal structures and produces localized surface plasmon resonances which enhance Raman scattering. In this embodiment, the grating layer 118 comprises of a planar metal, such as gold or silver, or a dielectric material. Suitable metal surfaces in accordance with the present disclosure include various noble metals, e.g. gold, silver, platinum, as well base metals such as copper, aluminum, chromium, and also various metal alloys, etc. The metal may be provided in the form of a film, preferably a thin film. In an additional embodiment, the grating 152 is made from non-metal material which produces local optical resonances which enhance light-matter interactions to produce large Raman scattering signal. One example of a non-metal dielectric optical resonance grating 152 is a guided-mode resonance structure that produces strongly enhanced near optical field which enhances the Raman scattering signal. In one embodiment, the nanostructures comprise periodic nanoholes 153. It is to be understood that the use of nanoholes 153 is merely exemplary and the repeating nanostructures may comprise the form of slits or any other repeating raised shape, such as raised circles or squares. The nanoholes 153 are arranged in a periodic, repeating fashion.

The excitation laser 150 excites the localized resonance (localized surface plasmon resonance or other localize optical resonance) of the nanostructures when the laser frequency is tuned close to the resonance frequency. The localized optical resonance creates a significantly enhanced optical field near the surface 155 of the nanostructures 153. The highly confined photons interact with the molecules near the nanostructure surface 154 and cause the enhanced Raman scattering with frequency shifts accordingly to the structure of any bound molecules. Because of the patterned diffraction grating, non-zeroth order diffractions 154, 156, 158, 160 may be produced. The shifted Raman scattering light 154, 156, 158, 160 propagates in different directions according to their wavelengths and the patterned grating period. Raman scattering spectra can be captured with a linear photodetector array 162 to measure the angularly dispersed diffraction. The excitation laser light 150 and the Raman scattering light 154, 156, 158, 160 are separated in different directions in non-zero order diffractions because they are at different wavelengths. A linear photodetector array 162 is used to capture the spatially dispersed surface enhanced Raman scattering signal light 154, 156, 158, 160. No optical rejection filters are required because the Raman excitation laser 150 propagates into a direction different from the diffractions of the Raman scattering light propagation 154, 156, 158, 160. As opposed to traditional Raman spectrometers, the presently disclosed Raman sensor does not need optical rejection filters to block the Raman excitation laser.

The spectral resolution of the presently disclosed integrated Raman spectroscopic sensors is dependent upon the power of the angular dispersion, the size of the photodetector pixel and the distance between the photodetector array 162 and the patterned nanostructure grating 152. The angular dispersion of the patterned nanostructure SERS spectrometer may be derived from the following equation:

$$\frac{d\theta}{d\lambda} = \frac{1}{\sqrt{P^2 - \lambda^2}} \quad (2)$$

where P is the diffraction grating period and the λ is the wavelength. The spectral resolution Δλ of the integrated Raman spectrometer is calculated with the following equation:

$$\Delta\lambda = \Delta x \frac{P}{d}\left[1 - \left(\frac{\lambda}{P}\right)^2\right]^{\frac{3}{2}} \quad (3)$$

where Δx is the size of the photodetector pixels and d is the distance between the nanostructure grating and the photodetector array. The spectral resolution can be very high if the diffraction grating period is slightly larger than the longest wavelengths to be measured.

The presently disclosed integrated Raman spectrometer sensor may utilize any of the previously described nanostructure gratings, specifically those described with reference to FIGS. 2, 3A, 3B, 4, 5, and 6. The Raman spectrometer sensors may employ arrays with nanostructures formed as nanoholes, nano-dots, nano-apertures or nanoslits with nanostructure feature sizes smaller than the wavelength of light to be measured. In addition, nanostructures may also be formed as slits, dashes or other inwardly protruding shapes, or as any outwardly projecting structures fixed to the grating surfaces.

EXPERIMENTAL

Figure 8:
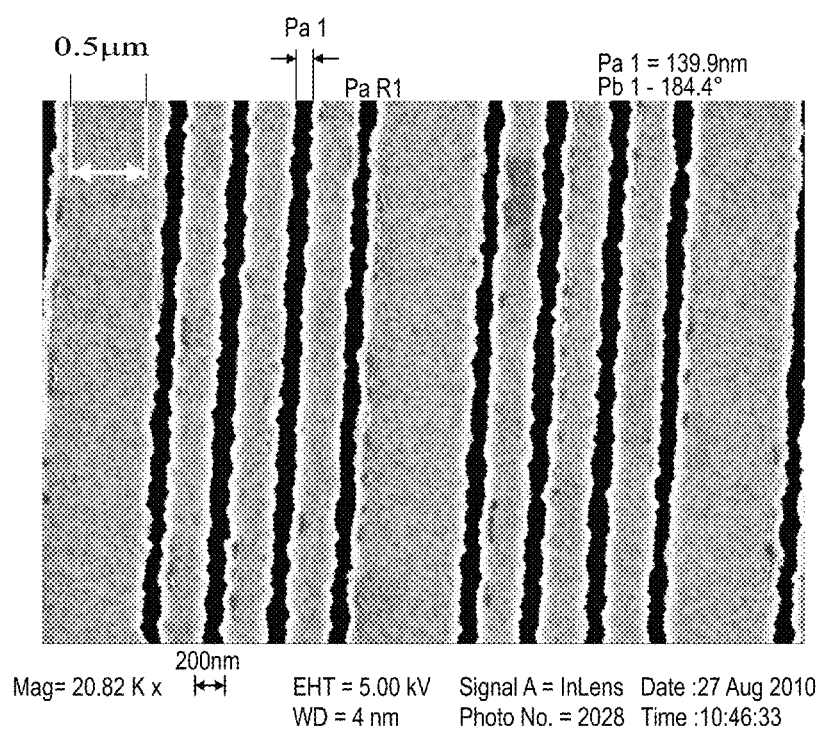
FIG. 8 shows a SEM picture of a super-period metal nanoslit grating.
Figure 9:
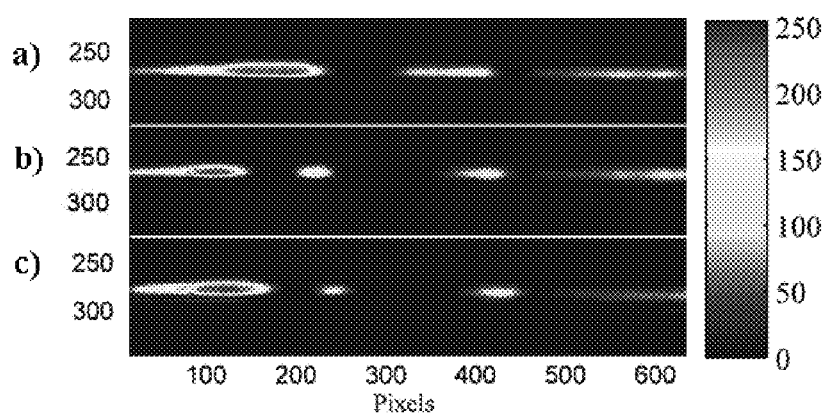
FIG. 9 shows a first order diffraction intensity distribution captured by a coupled charge device (CCD) photodetector array when the super-period nanoslits device was exposed to air, methanol and acetone.

Nanoslit Structure
  Fabrication
  A super-period nanoslit grating made in a thin gold film on a quartz wafer surface was fabricated by use of a standard e-beam lithography process. A 2 nm thick chromium adhesion layer and a 60 nm gold film layer were sputtered onto a quartz substrate using the magnetron DC sputtering technique. A 200 nm electron beam resist layer was then deposited on top of the gold film by spin coating. The nanoslit pattern was patterned in the e-beam resist layer using the e-beam lithography and then developed with an e-beam resist developer. After development, reactive ion etching was utilized to transfer the e-beam resist pattern to the gold film, followed by the removal of the e-beam resist. FIG. 8 shows the SEM picture of the fabricated super-period nanoslits. The nanoslit width is 140 nm in the 60 nm thick gold film. The small nanoslits period is 420 nm while the large period is 2100 nm.
  Testing
  The nanostructure array was tested with a broadband coherent light source. The broadband light source is a super continuum broadband laser with a spectrum range of 500 nm to 2400 nm wavelength. At normal incidence, the angular dispersion of the first order diffraction is measured with a CCD. The polarization of the incident light is perpendicular to the metal nanoslits so that localized surface plasmon resonance can be excited. FIG. 9 shows the angularly dispersed first order diffraction optical intensity distribution captured by the CCD, (a) with air on the surface, (b) with methanol liquid on the surface, and (c) with acetone liquid on the surface. The horizontal and vertical numerical numbers in the figure represent the pixels on the CCD.

The correspondence between the wavelengths and the pixels on the CCD must first be calculated in order to obtain the surface plasmon resonance spectrum. For the first order diffraction at the normal incidence, the diffraction angle is related with the wavelength (λ) and the super grating period (P) as $$\sin(\theta) = \frac{\lambda}{P} \quad (4)$$

By measuring the diffraction angle of a Helium-Neon (HeNe) laser at 632.8 nm, the spectrometer setup can be calibrated to find the correspondence between the wavelengths and pixels on the CCD. Once the correspondence between the wavelengths and the pixels on the CCD is found, one may plot the surface plasmon resonance measured in the first order diffraction vs. the wavelength.

Figure 10A:
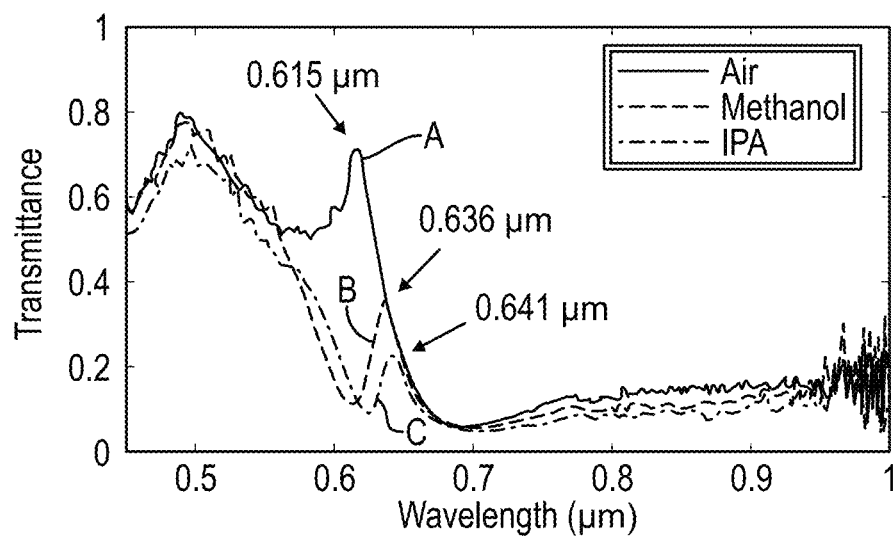
FIG. 10A illustrates a measurement of surface plasmon resonance in the super-period nanoslit grating from the zeroth-order transmission.
Figure 10B:
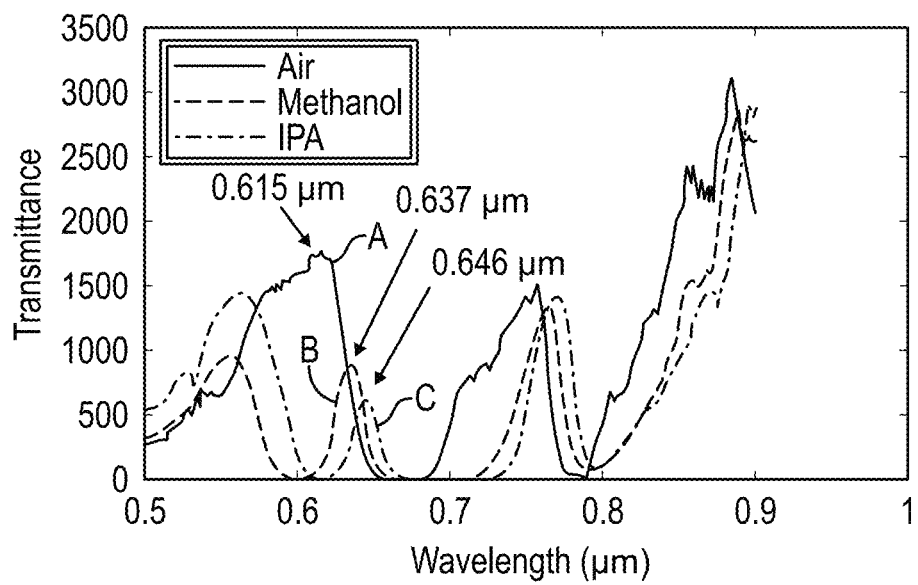
FIG. 10B illustrates a measurement of surface plasmon resonance in the super-period nanoslit grating from the first-order diffraction.

Methanol and acetone, with the refractive index of 1.3284 and 1.3586, respectively, were used to test the integrated surface plasmon chemical sensor. FIG. 10A shows the zeroth order transmission spectra from the device in the air (A), and after application of methanol (B) and acetone (C) onto the device surface. Acetone was applied after the measurement with methanol was complete and the methanol was completely vaporized. The zeroth order transmission spectra in FIG. 10A were measured using a commercial optical spectrometer. FIG. 10B shows the first order diffraction spectra measured with the super-period nanoslits sensor when (1) the device was exposed to the air (A), (2) methanol solution is applied on the device surface (B), and (3) acetone solution is applied on the nanoslits surface (C). The arbitrary unit used for the first order diffraction signal in FIG. 6B corresponds to the intensity levels measured by the CCD. It can be seen that the surface plasmon resonance in the super-period nanoslits at the wavelength of 0.616 micron can be captured by the CCD in the first order diffraction. The resonance wavelength shifts from 0.616 micron in the air to 0.637 micron when methanol is applied, and shifts to 0.646 micron when acetone is applied later. The small difference of resonance wavelengths measured with the external optical spectrometer and the integrated spectral sensor is within the uncertainty range of the external optical spectrometer. The spectral resolution of the commercial optical spectrometer used in the experiment is 2.0 nm. The spectral resolution of the integrated surface plasmon sensor is 0.7 nm, calculated from the angular dispersion of the super-period grating at 0.615 micron wavelength, the pixel size (5.6 micron) on the CCD, and the distance (14.5 mm) between the nanoslit device and the CCD.

Significantly, the demonstrated new surface plasmon sensor does not rely on an external optical spectrometer to measure the surface plasmon resonance and the resonance shift. The super-period metal nanoslit array itself supports localized surface plasmon resonance and performs the spectral analysis simultaneously.

Nanohole Structure
  Fabrication
  A super-period nanohole array device was fabricated in a 50 nm thick gold film on a quartz wafer with a standard e-beam lithography patterning and reactive ion etching process. This device is illustrated in FIG. 2. The device comprises a small nanohole array period p and a large grating period P. The large grating period P is five times of the small period p.

Figure 12:
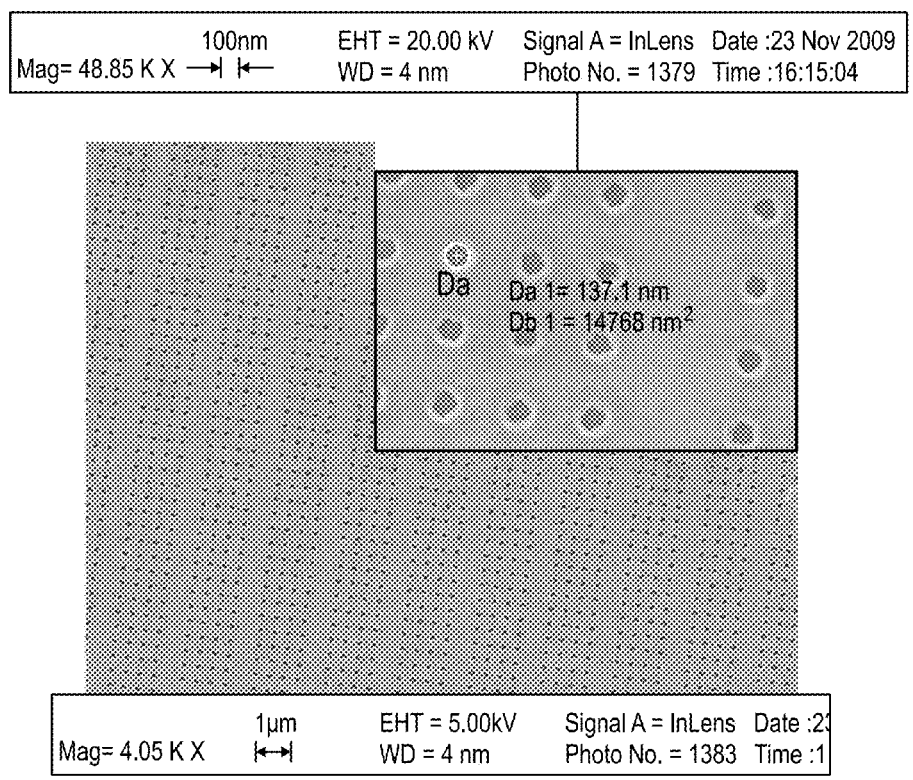
FIG. 12 shows a SEM picture of an e-beam patterned super-period nanohole array grating in a thin gold film.

The super-period nanoholes have a small period of 420 nm and a super grating period of 2100 nm. The SEM picture of the e-beam lithography patterned super-period metal nanohole grating is shown in FIG. 12. The diameter of the nanoholes in the array is approximately 140 nm.

Testing

Figure 11:
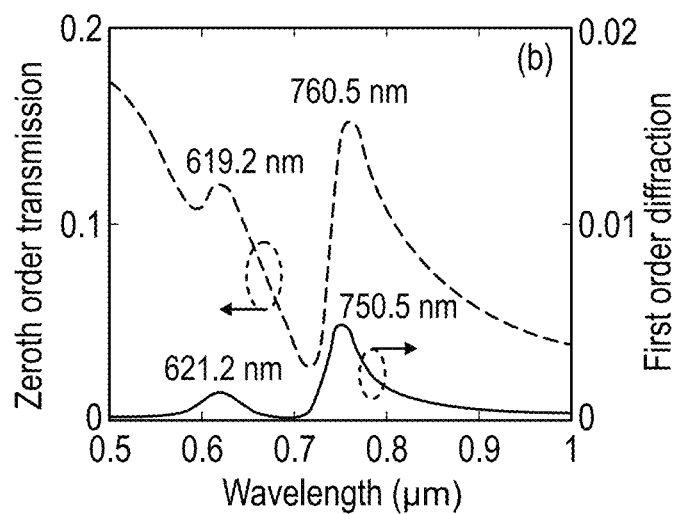
FIG. 11 illustrates calculated zeroth order transmittance and first order diffraction from a super-period metal nanohole array grating.

The zeroth order light transmission and the first order diffraction from the device were calculated with the normal light incidence. The polarization of the incident light is along the effective nanohole array grating lines, which is normal to the direction of diffractions. Calculations were carried out using a finite difference time domain (FDTD) software code. FIG. 11 shows the calculated zero-order transmission spectrum (dashed line curve) and the first order diffraction spectrum (solid curve) from the super-period nanohole array device. It can be seen that two plasmon resonance modes are excited in the device. The resonance at the longer wavelength corresponds to the tightly confined surface plasmon mode. The resonance at the shorter wavelength corresponds to the weakly confined surface plasmon mode. FIG. 11 illustrates that the zeroth order transmission peak due to the tightly confined plasmon resonance mode is at 760.5 nm wavelength and the first order diffraction peak due to the same plasmon resonance mode is at 750.5 nm wavelength.

FIG. 11 illustrates that the surface plasmon resonance in the super-period nanohole array can be observed in the zeroth order transmission and also in the first order diffraction. However, resonance peak wavelength in the first order diffraction is slightly blue-shifted from the resonance peak wavelength in the zeroth order transmission. To gain understanding on the resonance, the electric field intensity distributions were calculated on a plane 20 nm above nanohole metal surface at 750.5 nm and 760.5 nm respectively. The results are illustrated in FIGS. 13A and 13B respectively. The electric field at 750.5 nm wavelength is stronger than the electric field at 760.5 nm wavelength in the near field. The electric field intensity versus the wavelength was calculated for the top center location of one of the two inner nanohole apertures within a super-period unit cell. The result is plotted in FIG. 14A. The strongest field enhancement at this location is at 750.5 nm wavelength. The electric field intensity versus the wavelength was calculated for the top center of one of the two outer nanohole apertures within a super-period unit cell. The results are plotted in FIG. 14B. The strongest field enhancement is at 749.5 nm wavelength. The first order diffraction peak wavelength of 750.5 nm is approximately the same as the near field resonance wavelength, although the near field resonance wavelength slightly varies with the location of measurement.

The red-shift of the zeroth order transmission peak wavelength from the near field resonance wavelength is due to the interference between the surface plasmon resonance radiations and the directly transmitted light through the nanohole thin metal film. A significant amount of light can transmit through a 50 nm gold film. The near field is strong due to the localized surface plasmon resonance. Therefore, the near field resonance wavelength is primarily determined by the local surface plasmon resonance. The far field diffractions, either the first order or higher orders, avoid the interference between the surface plasmon radiations and the transmission near the nanohole structure metal film. Therefore, the resonance in diffractions is directly related to the near field resonance.

Measurement

Figure 15:
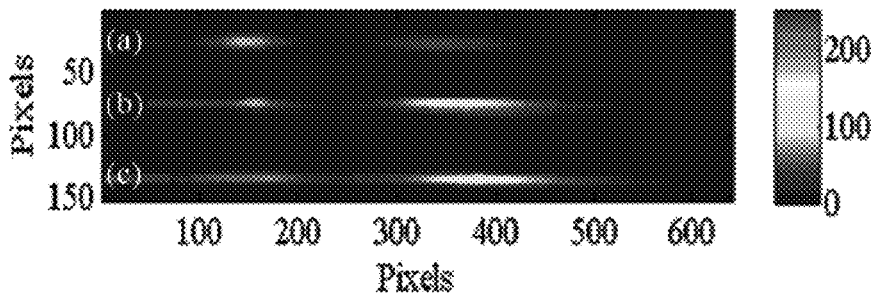
FIG. 15 shows spatially dispersed first order diffraction images captured by a CCD when the super-period metal nanohole array grating area was exposed to air, methanol and isopropyl-alcohol.

The super-period nanohole array device was measured with a super continuum broadband laser source. The excitation light was normally incident from the substrate with the polarization parallel to the nanohole effective grating lines. A CCD was used to capture the angularly dispersed intensity distribution of the first order diffraction from the nanohole grating. FIG. 15 shows the spatially dispersed first order diffraction intensity distribution when different liquid chemicals were applied to the device surface. A calibration is needed to obtain the correspondence between the CCD pixels and the wavelengths and to calculate the first order diffraction spectrum. A HeNe laser of 632.8 nm wavelength was used to calibrate the measurement setup. The HeNe laser was aligned to propagate in the same direction as the broadband laser. The pixel that corresponds to 632.8 nm wavelength on the CCD was first identified. Once the pixel corresponding to 632.8 nm wavelength is known, the correspondence between all pixels on the CCD and wavelengths can be obtained by using the diffraction equation $$\sin(\theta) = \frac{x}{\sqrt{d^2 + x^2}} = \frac{\lambda}{P} \tag{5}$$

where $\theta$ is the first order diffraction angle, x is the distance between the first order diffraction spot and the zeroth order transmission spot on the CCD, d is the distance between the nanohole grating device and the CCD, P is the super grating period, $\lambda$ is the free space wavelength corresponding to x. The distance d is 14.8 mm in the experiment setup. After the calibration, the first order diffraction can be obtained by normalizing the CCD signal with the responsivity of the CCD photodetector.

FIG. 15, line (a) shows the angularly dispersed first order diffraction image (diffracted along the horizontal axis) captured by the CCD when the device is in the air. Line (b) shows the spatially dispersed first order diffraction image captured by the CCD when methanol liquid is applied to the device surface. Line (c) shows the spatially dispersed first order diffraction image when isopropyl-alcohol is applied to the device surface. The images are the intensity signals captured by the CCD. The indexes of refraction of methanol and IPA liquids are 1.328 and 1.375, respectively.

Figure 16A:
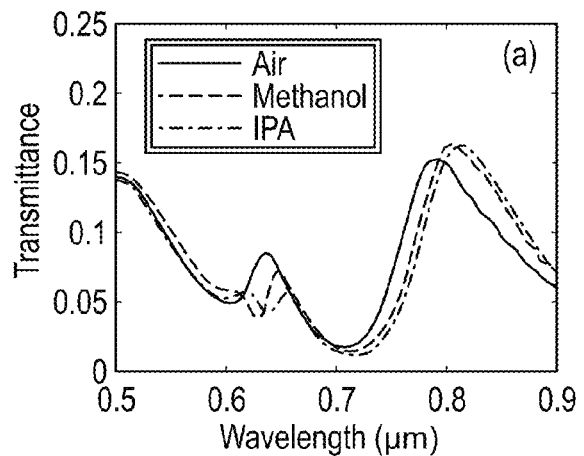
FIG. 16A is a graph showing measured zeroth order transmission spectra measured by using a commercial spectrometer.
Figure 16B:
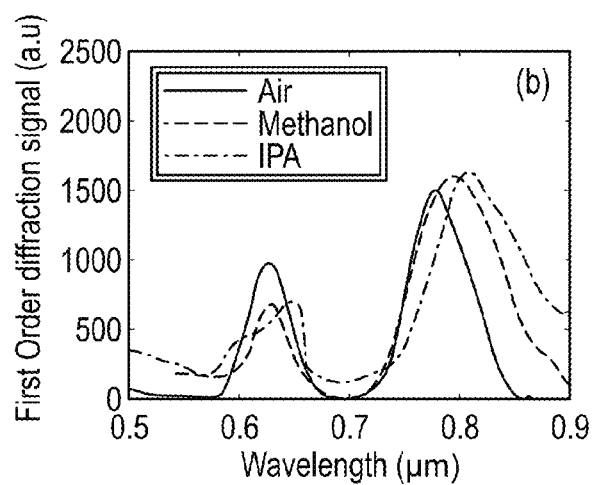
FIG. 16B is a graph showing measured first order diffraction spectra obtained with the disclosed surface plasmon resonance spectrometer.

FIG. 16A shows the zeroth order transmission spectra when different liquid chemicals are applied to the nanohole device surface. The resonance peak wavelength of the stronger resonance at the longer wavelength in the zeroth order transmission is 790 nm when the device exposes to the air (A). The resonance peak wavelength shifts from 790 nm to 804 nm when methanol is applied (B), and shifts again to 814 nm when isopropyl alcohol (IPA) is applied (C). FIG. 16B shows the first order diffraction spectra when different liquid chemicals are applied to the device. The spectra in FIG. 16B are measured by the CCD and normalized to the spectrum of incident broadband light source. The vertical axis in FIG. 16B has an arbitrary unit. When chemicals are applied to the device surface, the peak diffraction wavelengths in the first order diffraction are shifted. Tracking the shift of the diffraction peak wavelength of the longer wavelength resonance, it is found that the first order diffraction peak wavelength shifts from 778 nm in the air to 794 nm in the methanol (B), and again shifts to 809 nm in the IPA (C).

The surface plasmon resonance spectrometer sensor can measure surface plasmon resonance from the spatially dispersed first order diffraction with a single shot CCD image capture. Surface plasmon resonance spectrometers based on the metal nanostructure gratings can perform the functions of surface plasmon resonance sensing and resonance spectral measurements simultaneously.

Now, therefore, the following is claimed:

1. A method of identifying substances in a sample containing one or more analytes, comprising:
    (1) providing an array comprising:
        (a) a substrate;
        (b) a grating layer adhered to the substrate, the grating layer having a plurality of grating structures fixed to the upper surface of the grating layer;
        (c) a plurality of nanostructures formed on the grating layer such that a local resonance field based on the nanostructures is generated when light is incident to the surface of the grating layer, wherein the nanostructures are spaced
            (i) with a first periodic pattern having a period which is greater than the wavelength of the light incident to the surface of the grating layer; and
            (ii) with a second periodic pattern having a period which is less than the wavelength of the light incident to the surface of the grating layer;
    (2) contacting the sample with one or more biomolecules attached to the grating layer; and
    (3) positioning the array such that the light is incident to the surface of the grating layer;
    (4) capturing the light via a sensor; and
    (5) identifying at least one substance in the sample based on a spectrum of the captured light.

2. The method of claim 1, wherein the detecting is performed with a photodetector array.

3. The method of claim 1, wherein the detecting is performed with a charged coupled device (CCD).

4. The method of claim 1, further comprising detecting a shift in the surface plasmon resonance or optical resonance associated with the sample, wherein the identifying is based on the detecting.

5. The method of claim 1, wherein the substrate comprises transparent material.

6. A method of detecting surface plasmon resonance of a sample containing one or more analytes, comprising:
    (1) providing an array comprising
        (a) a substrate comprising a transparent material;
        (b) a grating layer adhered to the substrate; and
        (c) a plurality of nanostructures formed on a surface of the grating layer such that a local resonance field based on the nanostructures is generated when light is incident to the surface of the grating layer, wherein the nanostructures are spaced
            (i) with a first periodic pattern having a size which is greater than the wavelength of the light incident to the surface of the grating layer; and
            (ii) with a second periodic pattern having a size which is less than the wavelength of the light incident to the surface of the grating layer;
    (2) contacting the sample with one or more biomolecules attached to the grating layer;
    (3) positioning the array such that the light is incident to the surface of the grating layer;
    (4) capturing the light via a sensor; and
    (5) identifying substances in the sample based on a spectrum of the captured light.

7. The method of claim 6, wherein the sensor is a photodetector array.

8. The method of claim 6, wherein the sensor is a charged coupled device (CCD).

9. The method of claim 6, further comprising detecting a shift in the surface plasmon resonance associated with the sample.

* * * * *